United States Patent [19]

Strian et al.

[11] Patent Number: 4,763,666

[45] Date of Patent: Aug. 16, 1988

[54] METHOD AND APPARATUS FOR DETERMINING THE THERMAL SENSITIVITY OF THE HUMAN PERIPHERAL NERVOUS SYSTEM

[75] Inventors: Friedrich Strian, Graefelfing; Rupert Hoelzl, Munich; Günther Galfe, Munich; Stefan Lauterbacher, Munich; Wilhelm Lehmann, Munich, all of Fed. Rep. of Germany

[73] Assignee: Max-Planck-Gesellschaft zur Foerderung der Wissenschaften e.V., Göttingen, Fed. Rep. of Germany

[21] Appl. No.: 854,694

[22] Filed: Apr. 22, 1986

[51] Int. Cl.[4] .................................................. A61B 5/00
[52] U.S. Cl. .................................... 128/742; 128/744; 128/399
[58] Field of Search ........................ 128/742, 399, 744

[56] References Cited

U.S. PATENT DOCUMENTS

| | | | |
|---|---|---|---|
| 3,533,397 | 10/1970 | Scher | 128/742 |
| 3,942,515 | 3/1976 | Servos et al. | 128/742 |
| 4,573,472 | 3/1986 | Ito | 128/399 |
| 4,585,002 | 4/1986 | Kissin | 128/399 |
| 4,653,507 | 3/1987 | Laudadio | 128/742 |

FOREIGN PATENT DOCUMENTS

| | | | |
|---|---|---|---|
| 2609415 | 9/1977 | Fed. Rep. of Germany | 128/742 |
| 2753109 | 6/1979 | Fed. Rep. of Germany | 128/742 |

OTHER PUBLICATIONS

Severin et al, Pain, vol. 21, Apr. 25, 1985, pp. 369–378.
Maher, Proc. IEEE Aust., vol. 41, No. 4, Dec. 1980, pp. 146–149.

Primary Examiner—Kyle L. Howell
Assistant Examiner—John C. Hanley
Attorney, Agent, or Firm—Spencer & Frank

[57] ABSTRACT

To determine the heat or cold sensation or pain threshold of a human being, a thermode is applied to the skin of the subject under investigation, and the temperature is varied until the subject feels pain. This pain threshold temperature is maintained for a predetermined period of time and then the subject is requested to adjust the temperature until the same sensation is felt. The pain threshold temperature values obtained by this "tonic" method may be verified or improved by a "phasic" method of applying thermal stimuli, wherein pulse-type thermal stimuli are applied with randomly varying spacings and with temperatures which vary randomly about the pain threshold temperature established by the tonic method.

16 Claims, 7 Drawing Sheets

METHOD AND APPARATUS FOR DETERMINING THE THERMAL SENSITIVITY OF THE HUMAN PERIPHERAL NERVOUS SYSTEM

BACKGROUND OF THE INVENTION

The present invention relates to medical methods and apparatus, and more specifically to a method and an apparatus for determining the heat and cold sensation and pain thresholds of the human nerve system.

Determining the temperature level at which a subject begins to feel a sensation or pain due to the application of a thermal (heat or cold) stimulus is becoming increasingly important for establishing the status of the so-called small or unmyelinated nerve fibres which comprise about 85% of all nerve fibres in the peripheral nerve system, and of various other body functions. For instance, it has been shown that the temperature sensitivity of a patient suffering on diabetes mellitus type I varies synchronously with the blood sugar level.

F. Strian et al describe in the West-German medical magazine "Der Nervenarzt", 1984, 55: 103–107 a method of determining the temperature sensation threshold by applying heat of controllable temperature by means of a heat applicator in the form of a Marstock thermode, which comprises a Peltier element. The temperature of the applied heat is progressively increased until the subject under investigation signals that he or she feels a heat sensation or pain, which he or she signals by pressing a button. This terminates the application of heat. A cold sensation or pain threshold may be determined by a similar procedure. Several threshold values obtained as described are averaged.

SUMMARY OF THE INVENTION

According to a first aspect of the invention, method and apparatus are provided for applying thermal (heat and/or cold) stimuli, which are automatically maintained at a constant temperature for a predetermined period of time after actuation of a control device. The control device is actuated, when the subject (patient) under investigation begins to feel the application of heat or cold, respectively or pain due to the thermal stimulus. The temperature at the time of actuation, and thus the temperature which is maintained for the predetermined period time, is recorded. After such period of time has elapsed, the subject is requested to set a new, second temperature level, which produces the same sensation as the stimulus applied first. If the first and second temperature values are equal, they indicate the real pain threshold. If (in the case of heat stimuli) the second value is higher than the first, the patient has adapted to the heat stimulus and this indicates that the first value is lower than the real pain threshold. If the second value is lower than the first, this indicates that the patient has sensitized, which indicates that the first value is above the real pain threshold. In the case of differing first and second temperature values, the approximate real pain threshold temperature can be obtained by averaging the first and second values, preferably by averageing a number of pairs of such values. A similar procedure is followed for establishing the pain threshold for cold stimuli. The above described method may be termed "sensitizing method" or "tonic method".

The pain threshold temperature values obtained by the above-described tonic method may still differ from the actual values due to subjective factors, such as fear of the patient or the desire of the patient to please the physician who makes the investigation, or by the desire to produce specific results. According to a second aspect of the present invention, which relates to a method, which may be called "phasic" method, such falsification of the results can be avoided by repeated application of thermic stimuli with different temperatures which vary around the estimated or approximately established pain threshold temperature in a manner not predictable by the patient. The pain threshold temperature is preferably established by the above described tonic method. Preferably the temperatures of the thermic stimuli vary essentially randomly with respect to the estimated or approximately established pain threshold temperature and/or the periods of time between subsequent thermic stimuli, during which periods some baseline temperature is applied, which does not cause pain, vary essentially randomly within predetermined ranges. The subject under investigation indicates whether a thermic stimulus has caused pain or not. In a preferred embodiment of the phasic method, the indication whether a thermal stimulus is above or below the pain threshold is obtained by objective means, i.e. by measuring the pulse rate or the muscle tension of the patient.

DESCRIPTION OF A PREFERRED EMBODIMENT

First, the tonic method will be described with reference to FIG. 1, which is a temperature (T, degrees centigrade) vs. time (t) diagram showing the variation of the temperature of the applied heat stimulus for two different pain threshold determination tests.

Between t1 and t2 the temperature T applied to the skin of the patient is raised from a start level (e.g. about 40° C.) until the patient indicates that he begins to feel pain. Then, the temperature is held constant for a predetermined period of time t2–t3, which is at least 30 seconds and generally no more than 120 seconds. A value of about 75 seconds is preferred at present.

Thereafter, the patient is requested to adjust the temperature so that he feels the same sensation as at t2, the initially established pain threshold temperature. This second temperature value is established on t4. Thereafter the temperature is actively reduced to the start level. The temperature is recorded as shown in FIG. 1.

Figure 1:
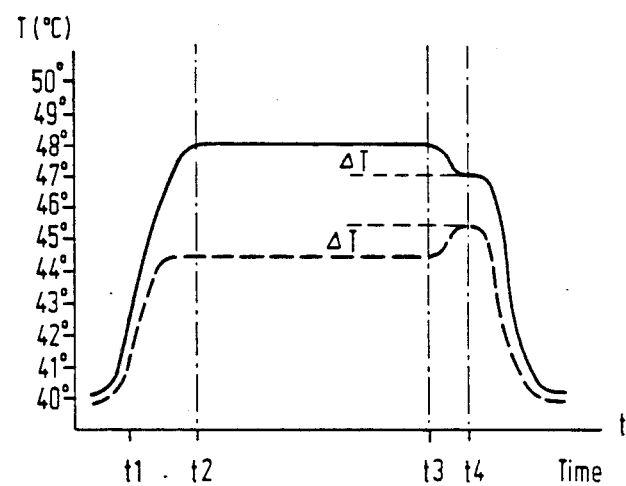
FIG. 1 is a diagrammatic depiction of an embodiment of the tonic method according to the invention.

A subject, who senses a decrease in heat intensity at the end of the period t2–te has adapted to the heat stimulus and consequently will increase the temperature of the applied heat, as shown in the lower, dashed curve of FIG. 1 between t3 and t4. (positive $\Delta T$ response). By contrast, a subject who senses an increase of heat has undergone a sensitation process and will decrease the temperature of the applied heat (negative $\Delta T$ response), as shown by the upper, solid curve of FIG. 1.

In a practical test, the heat stimuli were applied to the thenar of the hand with a Marstock thermode (contact area 20×30 mm, contact pressure 10p/cm$^2$). This device is based on the Peltier principle and heats up or cools down depending on the direction of the DC current that is passed through its semiconductor junctions.

The temperature at the thermode-skin interface is measured by a copper-constantan thermocouple glued to the thermode's surface and is continuously recorded by a pen recorder. With this arrangement, a very close approximation to tissue temperature at the side of the stimulated thermoreceptors and nociceptors of the skin is obtained.

Figure 2:
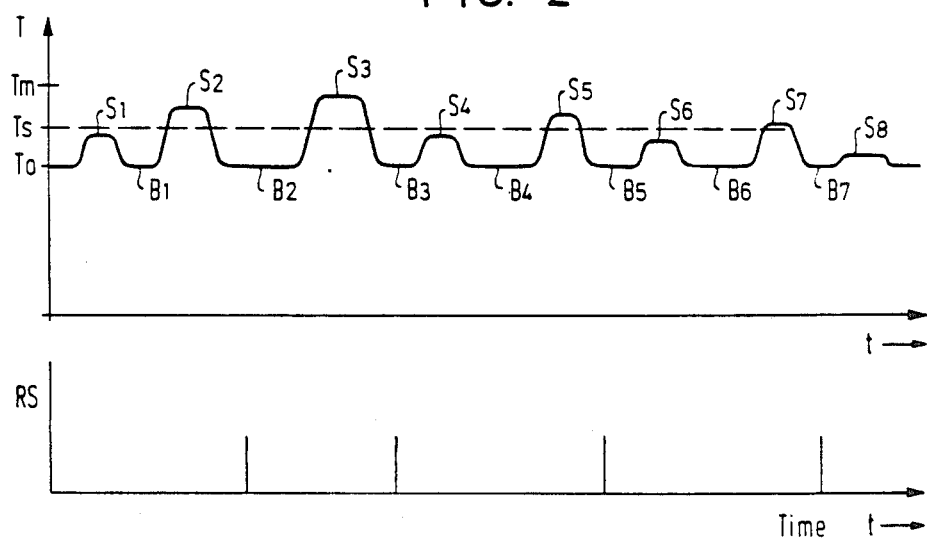
FIG. 2 is a diagrammatic depiction, not to scale, of an embodiment of the phasic method according to the invention.

An example of a measuring cycle of the phasic method is shown by the temperature (T) vs. time (t) diagram of FIG. 2. First, a basic temperature level TO is chosen which does not exceed the pain threshold. The basic temperature level is preferably the temperature $T_R$, which the thermode attains passively (i.e. without flow of electrical current) by temperature controlled water passed through it. Further, a pain threshold temperature is estimated or preferably determined by the tonic method explained with reference to FIG. 1. A sequence of stimulus temperature levels are chosen, which vary about the pain threshold temperature in a manner not predictable by the subject under investigation.

The upper diagram of FIG. 2 shows an exemplary sequence of heat stimuli S1 to S8, during which heat of elevated temperature is applied, and intervening intervals B1 to B7, during which the basic temperature TO is applied. The temperature levels of the thermal stimuli S1 to S8 vary more or less randomly, between the basic temperature TO and a limit temperature Tm, around the estimated or measured pain threshold temperature. The limit temperature Tm, which must not be exceeded for safety reason, may be a maximum temperature of about 50° C. in case of heat stimuli or a minimum temperature of about 5° C. in case of cold stimuli. The duration of the thermal stimuli may be about 2 to 5 seconds, and the duration of the intervals B1 to B7 may vary randomly between about 10 seconds and 30 seconds.

The application of each thermal stimulus S1 to S8 may be signalled by an acoustical and/or optical signal. The subject under investigation indicates after each thermal stimulus, whether the stimulus was above or below the pain threshold. These responses RS are recorded (lower diagram of FIG. 2) together with the temperature variation (upper diagram of FIG. 2). The actual pain threshold temperature Ts can be determined quite exactly by this procedure.

Figure 3:
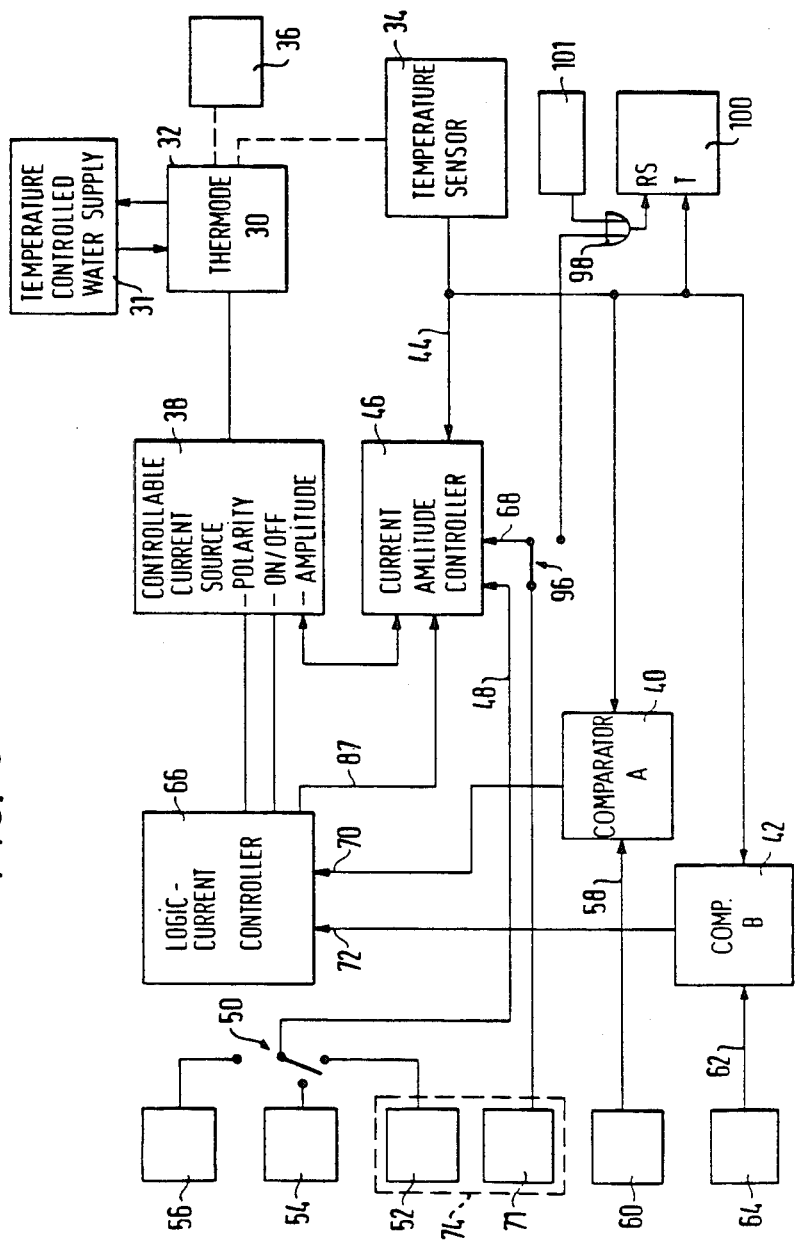
FIG. 3 is a block diagram of a preferred apparatus for performing the methods of the invention.

FIG. 3 is a block diagram of a preferred embodiment of an apparatus for pain level establishment according to both the tonic and the phasic methods described above.

The apparatus of FIG. 3 comprises a commercially available Marstock thermode 30, which includes a Peltier element and is used as applicator for thermal (heat or cold) stimuli. The thermode 30 is connected in series with a temperature controlled water supply 31 in a liquid circulation system and has a contact surface 32, which is heat coupled to a temperature sensor 34, comprising e.g. a thermocouple and built-in ice-point (0° C.) temperature reference, and to, for example, the thenar of a hand of a subject under investigation, shown schematically by block 36. The regulated temperature $T_R$ of the water supply or bath may be, for example, 30° C., and is used as reference temperature for the thermal stimuli, as will be explained with reference to FIGS. 9 and 10. The contact surface is covered with a thin electrically insulating layer (not shown) made of a material of relatively high thermal conductivity, as BeO or Al$_2$O$_3$.

The thermode 30 is supplied with direct current pulses of controllable duration, amplitude and polarity from a controlled current source unit 38 which will be described in more detail below with reference to FIG. 4. An actual temperature signal output of a temperature sensor 34 is coupled to first inputs of first (A) and second (B) comparators 40 and 42, respectively, and a first input 44 of a current amplitude controller 46. A second input 48 of the current amplitude controller 46 receives an analog signal representing a desired temperature level from a mode selection switch 50, which allows selection of one of three variable reference temperature signal sources, namely a control device 52 actuable by the subject under investigation, a control device 54 actuable by the physician, who conducts the test, and a programming device 56, which may comprise a computer and a digital-analog-converter (not shown), or any other programmable signal source.

Comparators 40 and 42 have their second inputs 58, 62 coupled to adjustable reference signal sources 60 and 64, respectively. The first and second comparators 40, 42, have output terminals coupled to corresponding input terminals 70 and 72, respectively, of a logic current controller unit 66, which will be described in detail below with reference to FIG. 6.

The control devices 52, 54, and the reference signal sources 60, 64 may each comprise a calibrated potentiometer connected across a stabilized voltage source (not shown).

The current amplitude controller 46 further has a second control input 68 coupled to a push-button switch 71 which may be mounted togehter with the control device 52 in a hand-held unit 74 schematically shown by a dashed rectangle.

A one-pole double-throw switch 96 allows coupling of push-button switch 71 alternatively with a first input of an OR gate 98 which has its output coupled to a first input of a multiple pen recorder 100, which allows the subject under investigation to record the responses RS (FIG. 2) by pressing the push-button switch 71. A second input of the OR gate 98 is coupled to an apparatus 101, e.g. a pulse sensor or a polygraph type device adapted to produce an output signal for objectively recording the responses of the subject to an applied thermal stimulus.

Figure 4:
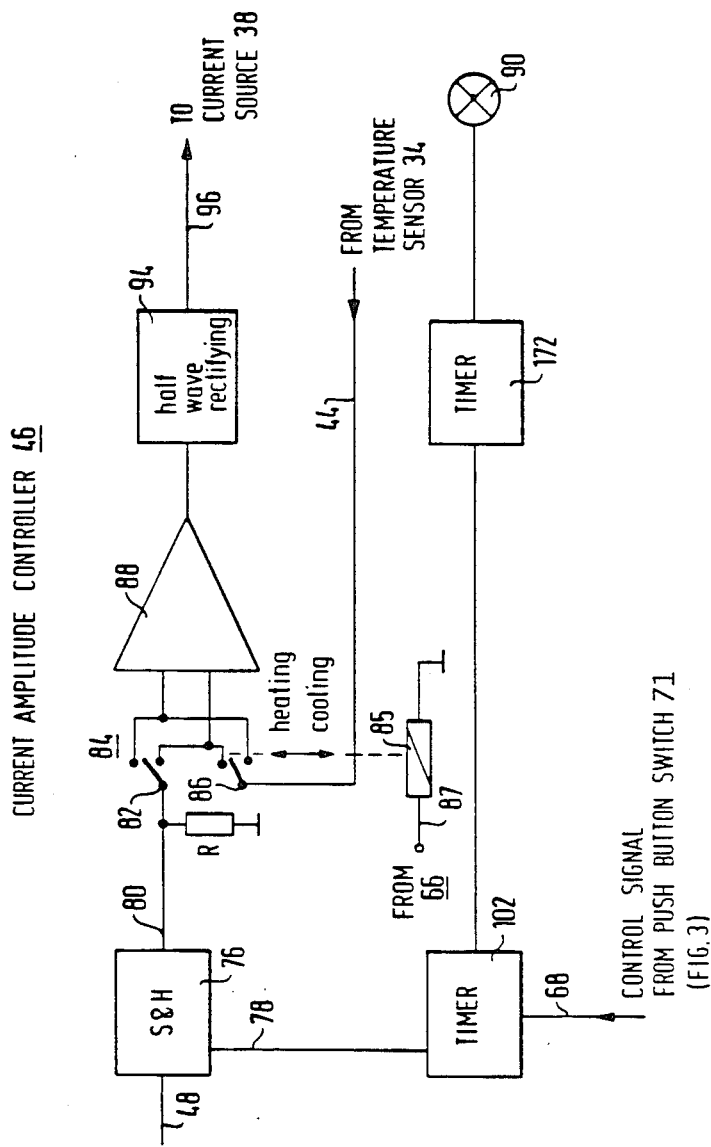
FIG. 4 is a more detailed diagram of a preferred embodiment of a current amplitude control unit of the apparatus of FIG. 3.

Reference is now made to the circuit diagram of the current amplitude controller 46 shown in FIG. 4. The input line 48 carrying the desired temperature signal is connected to an input terminal of a sample and hold (S&H) circuit 76 which has a control input terminal 78 and an output terminal 80. The output terminal 80 is coupled to a first input terminal 82 of a two-pole double-throw switch 84. A second input terminal 86 of switch 84 is connected to the actual temperature signal output 44 of the temperature sensor 34. A first and second pair of output terminals cooperating with the input terminals 82 and 86 are coupled to the inputs of a differential amplifier 88 as shown to form a polarity reversal switch, which secures the correct polarity of the difference between the actual and desired temperature signals across the input terminals of the differential amplifier for both the heating and cooling modes of operation. The differential amplifier 88 has its output coupled via a half-wave rectifier circuit 94 to an amplitude control input 96 of the controlable current source 38 which will be described in more detail with reference to FIG. 5.

The control input 78 of the S&H circuit 76 is coupled to a first output of a timer 102. The timer 102 may comprise a monostable multivibrator and means to preset the duration of the period of time which the multivibrator remains in its actuated state after having been triggered by a trigger signal received at a control input 68 coupled to the push-button switch 71.

Timer 102 has a second output coupled to a second, similar timer 172, which is triggered when the timer 102 switches back to its normal state. Timer 172, when triggered, energizes a signal lamp 90 or other optical or acoustical signalling device, such as a buzzer, for a predetermined period of time, to alert the patient to readjust the temperature control device 52 as explained with reference to FIG. 1.

Figure 5:
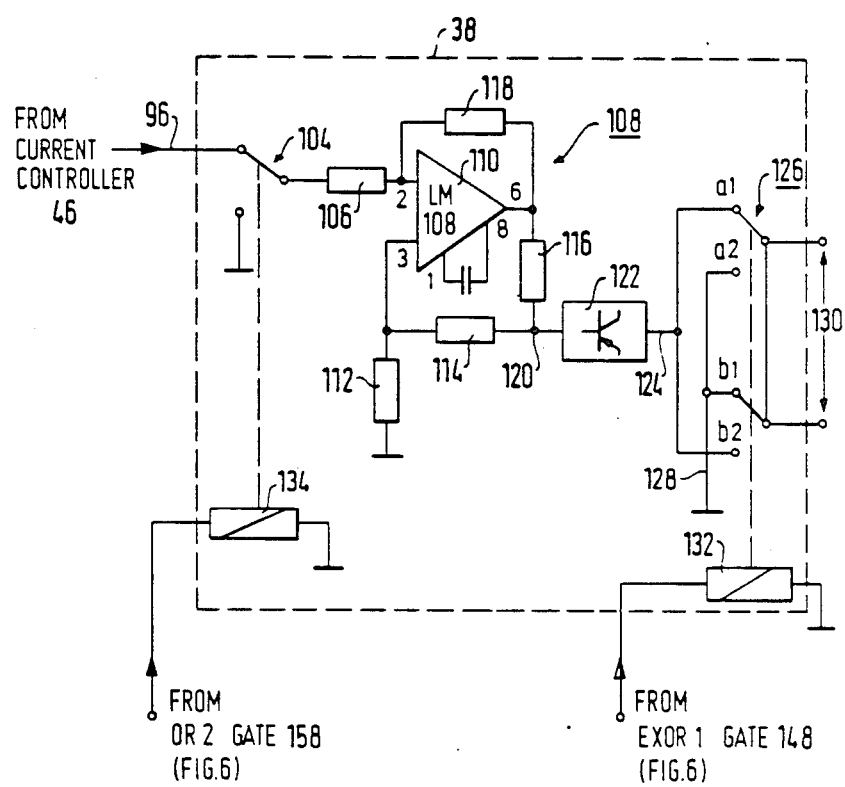
FIG. 5 is a more detailed diagram of a preferred embodiment of a controllable current source of the apparatus of FIG. 3.

The controllable current source 38 shown in FIG. 5 comprises a single-pole double-throw switch 104 which receives a current amplitude control signal from the output 96 of the half-wave rectifier of the current controller 46. A second input terminal of switch 104 is connected to ground. An output terminal of switch 104 is coupled to an input resistor 106 of a current source circuit 108 which supplies, at an output terminal 120 an output current proportional to the input voltage applied to the input resistor 106. The input resistor 106 is coupled to a first input of an operational amplifier 110 (type LM108, National Semiconductor, Santa Clara, Calif.). A second input of the operational amplifier 110 is coupled through a resistor 112 to ground and through serially connected resistors 114, 116 to an output terminal of the operational amplifier. A negative feed-back resistor 118 is coupled between the output and the first input of the operational amplifier 110. The junction 120 of the resistors 114, 116 forms the output terminal of the current source circuit 108.

A linear current power amplifier 122 has its input connected to the output junction 120. The output of the power amplifier 122 is coupled to a first input terminal 124 of a current polarity reversal switching device 126 which has a second input terminal 128 connected to ground. The switching device 126 comprises a double-pole double-throw switch and has two pairs of input terminals a1, a2 and b1, b2, selectively and alternately engageable by movable contacts connected to output terminals 130, across which the thermode 30 (FIG. 3) is connected.

The switching device 126 may be an electromagnetic relay switch and has an actuating device 132 which is controlled by a first output from the logic current controller 66 (FIG. 3). Switching device 84 including the actuating device 85 (FIG. 4) also may be an electromagnetical relay. The switch 104 may be likewise an electromagnetic relay and comprises a control device 134 which is controlled by a further output from the logic current controller 66.

Figure 6:
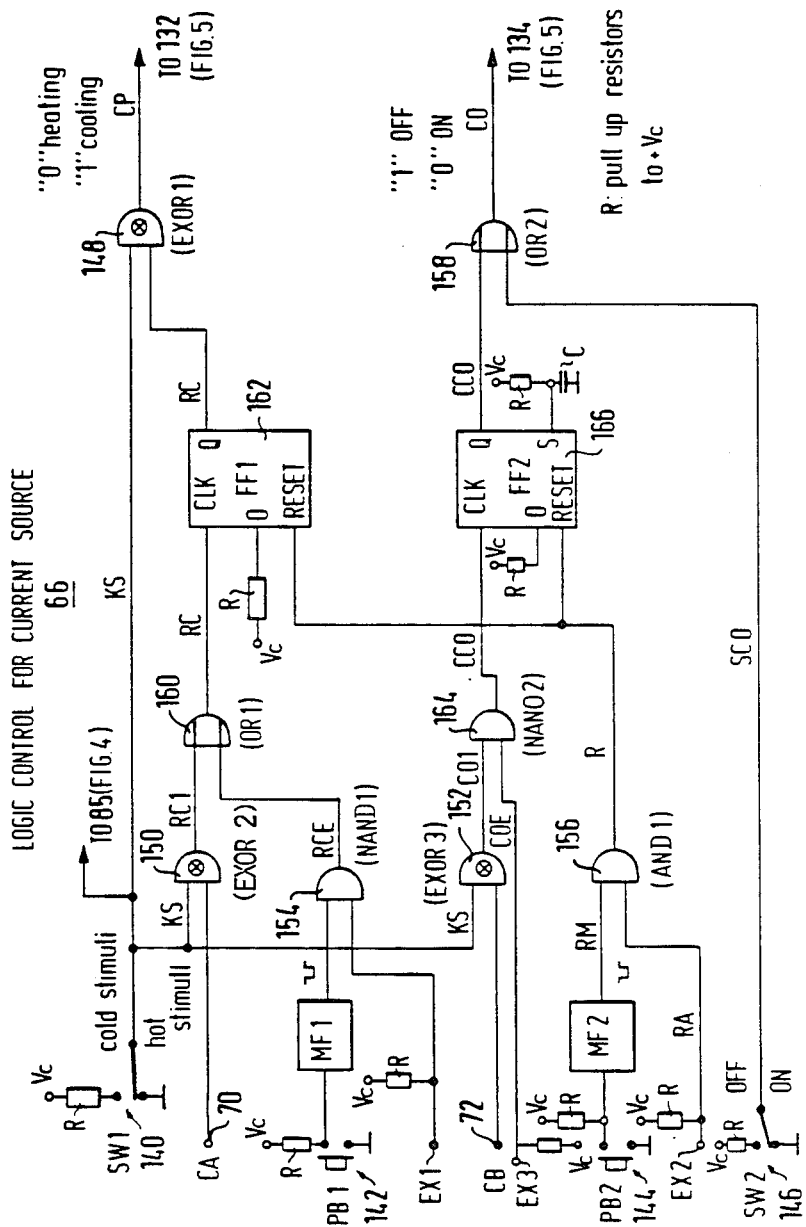
FIG. 6 is a diagram of a preferred embodiment of a logic current control unit of the apparatus of FIG. 3.

The logic current controller 66 shown in detail in FIG. 6 allows selection of whether hot or cold stimuli are applied, and provides the necessary logic control of the controlled current source 38 (FIG. 5).

More specifically, the unit 66 comprises a plurality of control elements which are actuable by the physician and are incorporated in a control panel (not shown). These control elements include
 a SW1 switch 140 for selecting hot or cold stimuli;
 a PB1 push button switch 142 which effects, upon actuation, a reversal of the current flowing through the thermode 30 (FIG. 3) and allows e.g. terminating a tonic stimulus (FIG. 1);
 a PB2 push button switch 144, which, when actuated, initiates the current flow through the thermode with the polarity selected by the SW1 switch 140.
 a SW2 switch 146, which is a main or emergency switch for turning the thermode current on and off.

The resistors R shown in FIG. 6 are "pull-up" resistors which secure the correct initial state of the various logic elements when the apparatus is put into operation.

SW1 switch 140 has a movable contact coupled to a first input of each of an EXOR1 gate 148, an EXOR2 gate 150, an EXOR3 gate 152 and the actuating device 85 of switch 84 (FIG. 4). The second input of EXOR2 gate 150 is coupled to the input terminal 70 and, thus, to the output of A comparator 40. The second input of EXOR3 gate 152 is coupled to the input terminal 72, and thus, to the output B comparator 42.

PB1 switch 142 is coupled via a debouncing monoflop MF1 to a first input of a NAND1 gate 154, the second input of which is coupled to an external control device EX1 (not shown) which may be part of the control device 56 (FIG. 3), and may provide time control signals for terminating each stimulus initiated by PB2 or EX2.

PB2 switch 144 is coupled through a debouncing monoflop MF2 to a first input of an AND1 gate 156, the second input of which is coupled to an external control device EX2 (not shown) which may be likewise implemented by the control device 56 (FIG. 3).

The ON-OFF SW2 switch 146 is coupled to a first input of an OR2 gate 158.

The ouputs of gates 150 and 154 are coupled to the inputs of an OR1 gate 160. OR1 gate 160 delivers, when activated, a RC signal (reverse current) to a clock input CLK of a FF1 flipflop 162, the Q output of which is coupled to the second input of EXOR1 gate 148. The output of EXOR3 gate 152 is coupled to a first input of a NAND2 gate 164, the second input of which is coupled to an external control device EX3 (not shown), which may be implemented by the control device 56 (FIG. 3). The output of NAND2 gate 164 is coupled to a clock input CLK of a FF2 flipflop 166, which, when set, produces an "OFF"-output signal CCO to a second input of OR2 gate 158. Flipflops 162 and 166 have their reset inputs coupled to the output of AND1 gate 156. FF2 Flipflop 166 has a pull-up resistor R and a capacitor C coupled to its preset input S to assure that the apparatus attains the OFF state of the thermode current after initially switching on of the apparatus.

The output of EXOR1 gate is coupled to the actuating device 132 (FIG. 5) which actuates the polarity reversing switching device 126 (FIG. 5).

The output of OR2 gate 158 is coupled to the actuating device 134, which controls the switch 104 (FIG. 5).

Figure 7:
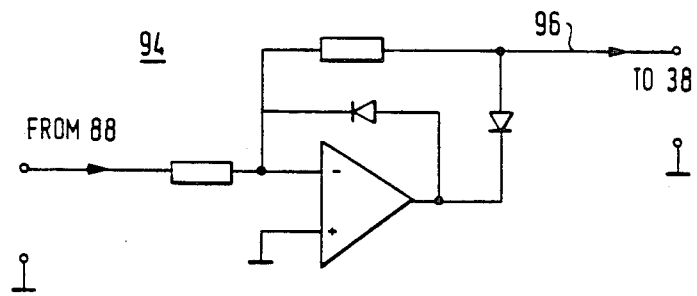
FIG. 7 is a diagram of a half-wave rectifier circuit useful in the circuit of FIG. 4.

The circuit diagram of the half-wave rectifier circuit 94 in FIG. 7 is self-explanatory. For a positive input voltage, the circuit shown produces a proportional negative output voltage; for an input voltage which is zero or negative, the circuit produces a zero output voltage.

Figure 8:
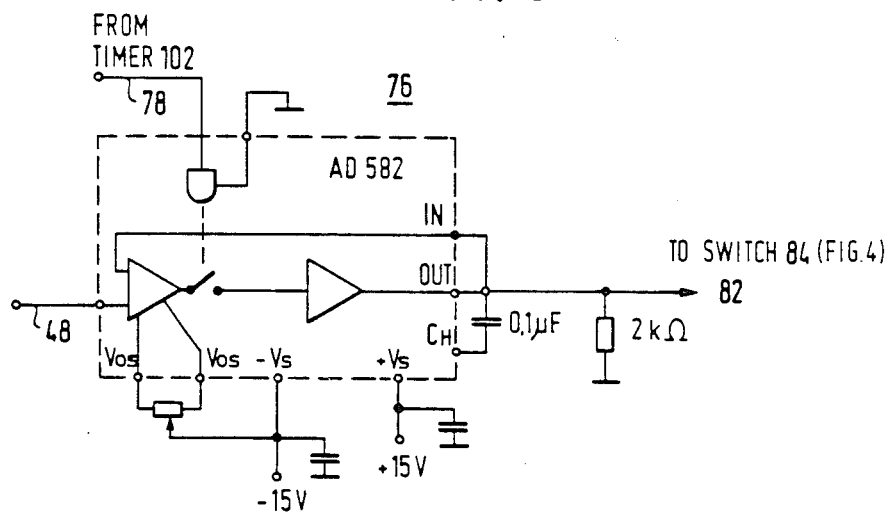
FIG. 8 is a diagram of a sample-and hold circuit useful in the circuit of FIG. 4.

The circuit diagram of the sample-and-hold circuit 76 shown in FIG. 8 is likewise self-explanatory. When timer 102 (FIG. 4) is triggered into its active state, it furnishes a "hold" signal to the control input 78 of the circuit 76 which then provides to the terminal 82 of switch 84 of the current amplitude controller 46 of FIG. 4 an output signal equal to the signal at its input 48; this signal is held as long as the timer 102 is in its activated state.

The operation of the apparatus of FIG. 3 will now be explained with reference to FIGS. 9 and 10 which are temperature (T) vs time (t) diagrams referenced to the thresholds of A comparator 40 and B comparator 42, and to the temperature $T_R$ of the water supply 31 (FIG. 3).

First, the desired mode of operation (heat stimuli or cold stimuli) is set on SW1 switch 140 (FIG. 6) by the physician. In case of a tonic mode of investigation, the mode switch 50 (FIG. 3) is set on control device 52. The threshold temperature TA of A comparator 40 is set by control device 60 to a maximum temperature or minimum temperature which the thermode must not exceed when applying heat or cold stimuli, respectively.

The threshold temperature TB of B comparator 42 is set by the control device 64 to a value which is slightly (e.g. 0.5° to 1° C.) below (heating mode, FIG. 9) or above (cooling mode, FIG. 10) the reference temperature $T_R$. The thermode 30 assumes passively the temperature of the water supply 31. It is checked whether the control device 52 is reset to the starting temperature level, which may be the water reference temperature $T_R$. Then, the test is initiated by pressing the PB2 push-button switch 144 (FIG. 6). This activates the current control and the temperature of the thermode 30 is brought actively to a value set on the control device 52.

Figure 9:
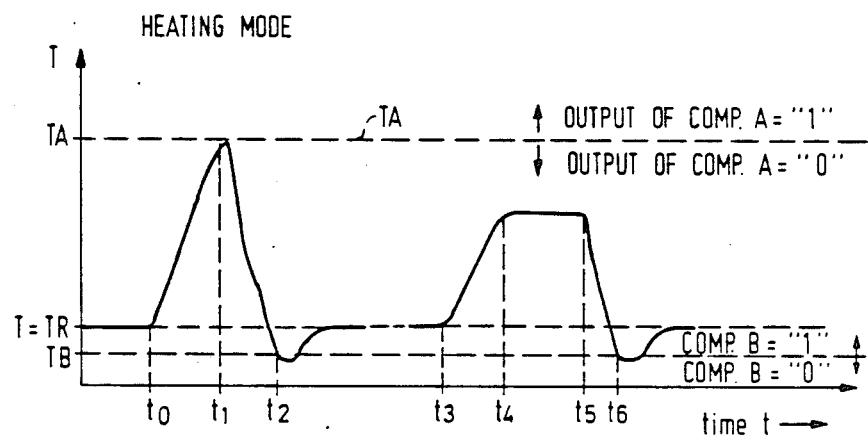
FIG. 9 and FIG. 10 are time diagrams for explaining the operation of the apparatus of FIG. 3 in a heat stimulus application mode and a cold stimulus application mode, respectively.

Referring to FIG. 9, if the temperature is raised excessively, as shown between $t_0$ to $t_1$, the A comparator 40 will change its state when the temperature of the thermode 30 exceeds the maximum temperature TA set by device 60. The change of the state of the output signal of A comparator 40 sets flipflop 162. The signal RC from the Q output of the flipflop 162 reverses the polarity of the current through the thermode by actuating the polarity reversal switching device 126 (FIG. 5), so that the temperature of the thermode is actively reduced during the interval $t_1$–$t_2$. When the temperature is decreased below the threshold temperature TB of B comparator 42, this comparator will change its state and its changed output signal will set the FF2 flipflop 166 which causes the switch 104 to change into the "OFF" state and cut-off of the current through the thermode 30. The current remains OFF until the flipflops 162, 166 are again reset by actuating the PB2 push-button switch 144.

In a normal tonic test, the apparatus is enabled by pressing PB2 switch 144, and the subject under investigation then raises the temperature of the thermode by appropriate actuation of control device 52 until she or he feels pain (period of time $t_3$ to $t_4$, FIG. 9). When pain is felt, the push-button switch 71 is actuated. This starts the timer 102. The test is then performed as described with reference to FIG. 1 and at the end of the test, the physician terminates the test by actuating PB1 switch 142 ($t_5$). This reverses the current flowing through the thermode 30, so that the thermode is actively cooled down between $t_5$ and $t_6$. At $t_6$ comparator B changes its state and switches the current off as explained above. The thermode attains then passively the temperature of the water supply 31.

Figure 10:
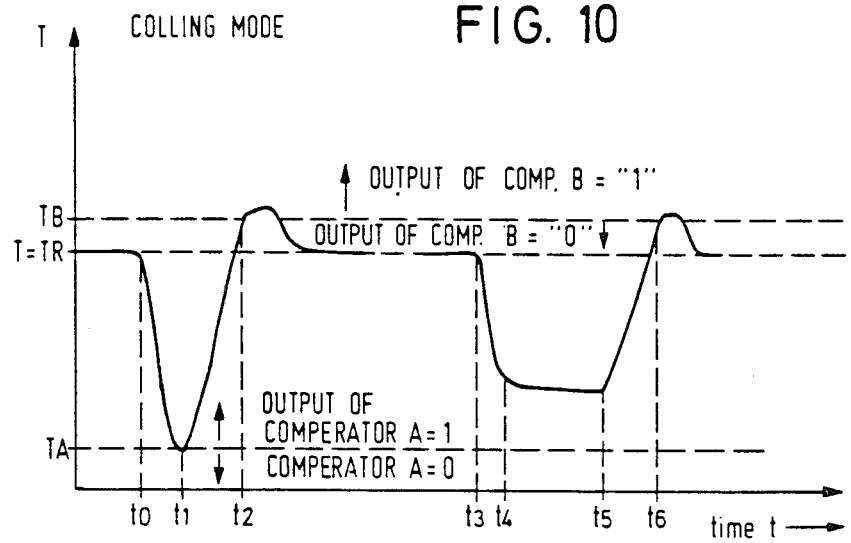

The cooling mode of operation shown in FIG. 10 is quite similar to the heating mode shown in FIG. 9; in fact FIG. 10 is a mirror image of FIG. 9 in respect to the reference temperature $T_R$. Thus, now further explanation should be necessary.

In a phasic test, the mode switch 50 is set on control device 56, which provides a desired temperature signal to current amplitude controller 46, a stimulus start signal at terminal EX2 (FIG. 6) and a stimulus end signal at terminal EX1 (FIG. 6) at the appropriate times to produce a randomized series of thermal stimuli as explaines with reference to FIG. 2.

In the manual mode of operation the mode switch 50 is connected to the control unit 54. The switch 96 is set to connect the push-button switch 71 to the recording device 100. The physician can now control the temperature through the control device 54. The actuation signal RS input of the recording device 138 may be alternatively or in addition connected to the sensing device 101 which automatically responds to some state of the patient, i.e. the muscle tonus or heart beat rate, to record an "objective" sensing signal.

It should be clear that various modifications and alterations could be made to the described embodiments, as using electronic switching devices and other types of circuits performing similar functions, within the scope and spirit of the present invention as set forth in the appended claims.

We claim:

1. An apparatus for testing the temperature sensitivity of a portion of the skin of a subject, said apparatus comprising:
    applicator means (30) having a contact surface (32) for directly applying, when energized, a thermal stimulus of controlled temperature to said skin portion;
    energizing means (38) connected to said applicator means for energizing said applicator means;
    controlling means (46, 52) connected to said energizing means for controlling said energizing means to establish a predetermined temperature of said contact surface of said applicator means;
    actuating means (71) for supplying an actuator signal; and
    maintaining means (76, 102) connected to said controlling means and being responsive to said actuating signal for maintaining essentially constant the temperature of said contact surface of said applicator means at a temperature value established by said controlling means at the time of actuation of said actuating means for a predetermined period of time after actuation of said actuating means (71).

2. The apparatus as claimed in claim 1, wherein:
    said applicator means comprises a Peltier element for producing said thermal stimulus;
    said energizing means comprises a controllable current source for energizing said Peltier element with a current of a level established by a temperature reference signal, said current source being responsive to said reference temperature signal and an actual temperature signal;

said controlling means comprises a manually adjustable reference signal source for providing said temperature reference signal to said current source;

said actuating means comprises a manually actuatable actuator element; and said maintaining means comprises a sample-and-hold circuit (76) and a timer (102) for storing said temperature reference signal and maintaining it for said predetermined period of time in response to the actuation of said actuator element.

3. The apparatus as claimed in claim 2, further comprising signaling means connected to said maintaining means (90) for signalling the expiration of said period of time.

4. The apparatus as claimed in claim 2, further comprising a temperature sensor fixed to said contact surface and an electrically insulating layer between said surface and said sensor, said temperature sensor providing said actual temperature signal.

5. The apparatus as claimed in claim 1, wherein said contact surface is provided with an electrically insulating coating.

6. An apparatus for testing the temperature sensitivity of a portion of the skin of a subject, said apparatus comprising:

applicator means (30) having a contact surface (32) for applying a thermal stimulus of controlled temperature to said skin portion;

energizing means (38) connected to said applicator means for energizing said applicator means; and controlling means (56) connected to said energizing means for controlling said energizing means to cause said applicator means to produce a series of timely spaced thermal stimuli each having a predetermined duration and a predetermined temperature, and the temperatures of said stimuli having values between a lower and an upper temperature limit;

varying means connected to said energizing means for varying each of said limits; and recording means connected to said applicator means for recording said temperature values and a response of said subject to selected stimuli.

7. The apparatus as claimed in claim 6, comprising signalling means to signal the application of a thermal stimulus.

8. The apparatus as claimed in claim 6, wherein said contact surface is provided with an electrically insulating coating.

9. The apparatus as claimed in claim 6, wherein said temperature values are essentially randomly distributed between said limits.

10. The apparatus as claimed in claim 6, wherein the time spacings of said stimuli vary in an essentially random manner.

11. The apparatus as claimed in claim 6, wherein said lower and upper limits are set below and above a preestablished level, respectively, at which said subject under investigation regards said stimulus as painful.

12. The apparatus as claimed in claim 6, further comprising actuating means actuated by a subject under investigation for signalling the subject's response to the thermal stimulus and wherein said recording means (100) records the times of actuation of said actuating means.

13. The apparatus as claimed in claim 6, further comprising response means (101), connected to said recording means, for deriving a physical response of the subject under investigation to the application of a thermal stimulus from said subject.

14. The apparatus as claimed in claim 6, comprising means for actively returning the temperature of said applicator means to a reference temperature level at the end of a thermal stimulus.

15. A method of establishing the sensitivity of a subject for thermal stimuli, said method comprising:

establishing predetermined upper and lower temperature limits; and applying thermal stimuli to a skin portion of said subject, said stimuli having temperatures which vary in an essentially random manner between said limits.

16. The method of claim 15, wherein said applying step includes applying said stimuli with varying time spacings.

* * * * *